United States Patent [19]

Wolf

[11] Patent Number: 4,524,066

[45] Date of Patent: Jun. 18, 1985

[54] PROCESS FOR THE PREPARATION OF INJECTABLE CHONDROITIN POLYSULFATE

[75] Inventor: Karl H. Wolf, Munich, Fed. Rep. of Germany

[73] Assignee: Luitpold-Werk Chemisch-pharmazeutische Fabrik, Munich, Fed. Rep. of Germany

[21] Appl. No.: 373,226

[22] Filed: Apr. 29, 1982

[30] Foreign Application Priority Data

May 11, 1981 [DE] Fed. Rep. of Germany ....... 3118588

[51] Int. Cl.³ ............................................. A61K 31/725
[52] U.S. Cl. ........................................ 514/23; 536/53; 536/118; 536/122
[58] Field of Search ........................ 536/53, 118, 122; 424/180

[56] References Cited

U.S. PATENT DOCUMENTS

| 2,767,167 | 10/1956 | Opie et al. | 536/114 |
| 2,803,558 | 8/1957 | Fronmuller | 536/114 |
| 2,959,583 | 11/1960 | Doczi | 536/53 |
| 3,174,904 | 3/1965 | Sawhill | 536/118 |
| 3,175,942 | 3/1965 | Anderson et al. | 536/118 |
| 3,405,120 | 10/1968 | Kawano et al. | 536/53 |
| 3,454,560 | 7/1969 | Nagasawa | 536/53 |

FOREIGN PATENT DOCUMENTS

| 870094 | 7/1949 | Fed. Rep. of Germany . |
| 935843 | 12/1955 | Fed. Rep. of Germany . |
| 968752 | 3/1958 | Fed. Rep. of Germany . |
| 1618857 | 3/1966 | Fed. Rep. of Germany . |
| 136572 | 7/1979 | Fed. Rep. of Germany . |

OTHER PUBLICATIONS

Karrer, et al., Zur Kenntnis Bluterennungs Hemmender Polysaccharid-Polyschwefel Säuer-Ester und Ahnticher Verbindung, Helv. Chim. Acta., 26, 1296, (1943).
Bergström–Über Polysaccharidesterschwefelsäuern mit Heparinwirkung–Hoope-Seyler's Zeitschrift fur Physiologische Chemie, 238, 163, (1936).
Chargaff et al., Studies on the Chemistry of Blood Coagulation, Journal of Biological Chemistry, 115, 155, (1936).
Piper, Toxicology of Synthetic Polysulphuric Acid Esters, Acta Pharmacol., 1946, 2, 317, 328.
Fransson, Periodate Oxidation of L-Iduronic Acid Residues in Dermatan Sulphate, Carbohydrate Research, 36, (1974).

Primary Examiner—Johnnie R. Brown
Attorney, Agent, or Firm—Cooper, Dunham, Clark, Griffin & Moran

[57] ABSTRACT

The invention relates to a process for the preparation of an injectable chondroitin polysulfate, which is characterized in that A a crude chondroitin polysulfate is depolymerized oxidatively, B the depolymerized chondroitin polysulfate is bleached, if necessary, with peracetic acid, C the product obtained after A or B is subjected once or twice to precipitation with methanol and/or ultrafiltration for fractionation with respect to molecular weight, D the product obtained after C is demineralized, if necessary, with cation exchangers, and E the product obtained after C or D is decolorized, if necessary, with active charcoal.

The invention furthermore relates to a chondroitin polysulfate which can be prepared by the above process. The invention also relates to a chondroitin polysulfate with an acute toxicity ($LD_{50}$), on intravenous administration, of >3,500 mg/kg in NMRI mice, of >3,000 mg/kg in Wistar rats, of >1,000 mg/kg in cats and of >1,000 mg/kg in dogs.

Finally, the invention relates to a pharmaceutical composition for human and veterinary medicine, characterized in that it contains a chondroitin polysulfate which can be prepared according to the above process of a chondroitin polysulfate with the above characteristics.

15 Claims, No Drawings

PROCESS FOR THE PREPARATION OF INJECTABLE CHONDROITIN POLYSULFATE

Both the preparation of chondroitin polysulfate, in particular the sulfation of chondroitin sulfate, and various ways of treating chondroitin polysulfate crude products with the aim of purification have been described in the prior art (S. Bergström, Hoppe-Seyler's Z. f. physiol. Chemie 238, 163; 1936—Chargaff, F. W. Bancroft J. biol. Chem. 115, 149, 155; 1936—Husemann et al. Z. Ges. Exp. Med. 114, 722; 1945—J. Piper Acta Pharm. Toxicol. 2, 317; 1946—P. Karrer, H. Koenig, E. Usteri, Helv. chim. acta 26, 1296; 1943—German Patent Specification 870,094—German Patent Specification 935,843—German Patent Specification 968,752—German Offenlegungsschrift 1,618,857—U.S. Pat. No. 3,454,560 and German Democratic Republic Patent Specification 136,572). However, none of these procedures leads to a satisfactory product.

The toxicity, which is still too high in spite of technical advances, and other disadvantages of chondroitin polysulfates according to the prior art as yet prohibit risk-free therapeutic use of these substances in the form of an injection.

The aim of the invention is therefore to obtain, in an economically advantageous manner, a highly pure chondroitin polysulfate in which the disadvantages of known chondroitin polysulfates are reduced to a minimum. It should be possible to use such a chondroitin polysulfate in the therapy of illnesses in humans and animals in any mode of administration.

The above aim is achieved by a process, the essence of which can be seen from the nature and sequence of the process steps which follow: oxidative depolymerization of a crude chondroitin polysulfate corresponding to the prior art, if necessary bleaching with peracetic acid, isolation of a fraction with a mean molecular weight of 5,000–15,000 by precipitation with methanol and/or ultrafiltration, if necessary demineralization by means of ion exchangers and if necessary treatment with active charcoal.

The invention thus relates to a process for the preparation of an injectable chondroitin polysulfate, which is characterized in that A crude chondroitin polysulfate is depolymerized oxidatively, B the depolymerized chondroitin polysulfate is bleached, if necessary, with peracetic acid, C the product obtained after A or B is subjected once or twice to precipitation with methanol and/or ultrafiltration for fractionation in respect of molecular weight, D the product obtained after C is demineralized, if necessary, with cation exchangers, and E the product obtained after C or D is decolorized, if necessary, with active charcoal.

The processes known from the prior art, for example those such as are described in the above-mentioned literature references, can be used for obtaining the crude chondroitin polysulfate used as the starting material. Without restricting the invention to this method or to one of the abovementioned methods of preparing crude chondroitin polysulfate, it is possible to start from a product which is obtained by sulfation of chondroitin sulfate with pyridine and chlorosulfonic acid. Chondroitin polysulfates of widely varying coloration can be used. It is also possible to use high-molecular chondroitin polysulfates originating from stage C of the present process.

The following reagents can be used to adjust the pH value in the process described below: acids such as inorganic acids, for example hydrochloric acid, and lower aliphatic carboxylic acids or peracids thereof, for example acetic acid or peracetic acid, and alkalis such as alkali metal hydroxide solutions, for example sodium hydroxide solution or potassium hydroxide solution. The individual steps of the process are preferably carried out under normal pressure. Unless otherwise indicated, the percentage data in the following text are "weight/volume" data. In the present process, methanol is given as the precipitating agent for intermediates and the end product. Other water-miscible organic liquids, such as, for example, ethanol, isopropanol, acetone, tetrahydrofuran and dioxane, are also similarly suitable. The intermediates produced in the individual steps of the process do not necessarily have to be isolated as dry substances. It is also possible to further process the solvent-moist masses without drying them. Salts in a concentration range of 0.1–10%, preferably 0.5–5%, are advantageously added during precipitation of the chondroitin polysulfate substances with water-miscible solvents. Salts which are particularly suitable are sodium or potassium chloride and sodium or potassium acetate.

The conditions for stages A to E of the process according to the invention which are described in more detail in the following text (page 8 paragraph 3 to page 16 paragraph 3) can be varied within a substantial range. Accordingly, the parameters given below for the individual stages are not to be understood as obligatory but only as an advantageous embodiment of the invention, so that the invention is not restricted to these parameters.

Chondroitin polysulfate can be depolymerized with hydrogen peroxide in the absence of heavy metals. The depolymerization step can be carried out in aqueous solution under the following conditions: the concentration of the crude chondroitin polysulfate can be 2–35%, preferably 10–20%. The concentration of hydrogen peroxide in the reaction medium can be 0.3–15%, preferably 1–5%. The reaction temperature can be 20°–100° C., preferably 50°–100° C. The reaction time is in the range from 10 minutes to 24 hours, preferably from 30 to 200 minutes. The pH value can be kept constant at between 3 and 9 or can also remain unadjusted, and is preferably between 4.5 and 7.

Heavy metals which are present can be blocked by complexing agents such as nitrilotriacetic acid, ethylenedinitrilotetraacetic acid, 1,2-cyclohexylenedinitrilotetraacetic acid, diethylenetriaminepentaacetic acid, 3,6-dioxaoctamethylenedinitrilotetraacetic acid or mixtures thereof or alkali metal salts thereof. The concentration of the complexing agent in the reaction medium is kept between 0.001 and 0.5%, preferably between 0.005 and 0.15%. When the reaction has ended, the reaction product can be precipitated with an excess of methanol, after addition of an alkali metal salt and either without cooling or after cooling, and isolated.

The depolymerization of chondroitin polysulfate with hydrogen peroxide can also be carried out in the presence of heavy metal salts, under particularly mild conditions. The depolymerization is carried out, for example, as follows: the concentration of the crude chondroitin polysulfate can be 2–35%, preferably 15–30%. The concentration of hydrogen peroxide in the reaction solution can be 0.5-15%, preferably 1-5%. The reaction temperature can be in the range from −10° C. to +80° C., preferably from 0° C. to 30° C. The reaction time can be in the range from 5 minutes to 24 hours, preferably from 30 to 500 minutes.

The pH value can be between 3 and 8, preferably between 4.5 and 7.5. Heavy metal salts which have proved suitable are inorganic and organic salts of iron, cobalt, copper, manganese and vanadium. The metals of these salts are preferably in the following valency levels: iron and cobalt: di- and tri-valent, copper: mono- and di-valent, manganese: di-, tri-, tetra-, hexa- and hepta-valent, and vanadium: di- and penta-valent. The concentration of metal salt is adjusted to between 0.001 and 0.5%, preferably between 0.05 and 0.2%. After the degradation, the pH value is adjusted to within the range from 5 to 14, preferably from 6 to 10, and the depolymerized product is isolated by precipitation with methanol.

The step of oxidative depolymerization of chondroitin polysulfate can be carried out by oxidative degradation of chondroitin polysulfate with peracetic acid in the presence of certain heavy metal salts with the same result as the above methods. The following conditions have been found to be those under which the reaction can be realized in an advantageous manner: the concentration of the crude chondroitin polysulfate can be 5-35%, preferably 10-25%. The concentration of peracetic acid in the reaction solution can be 0.1-7%, preferably 0.5-2%. The heavy metal salt concentration can be within the range from 0.001 to 0.5%, preferably 0.005 to 0.2%. The reaction temperature can be −10° C. to +90° C., preferably 0° C.-30° C. The reaction time can be within the range from 5 minutes to 24 hours, preferably from 15 minutes to 500 minutes. The pH value can be 2-12, preferably 3-8.

The reaction proceeds at a good rate, for example, with inorganic or organic salts of the following heavy metals: iron, cobalt, copper, manganese and vanadium. As regards the valency of the metals in these metal salts, the statements made above for depolymerization with hydrogen peroxide apply. It may be advisable to stop the depolymerization operation by means of a chelating agent, such as, for example, ethylenedinitrilotetraacetic acid or other metal-blocking agents, especially in the case of relatively short reaction times. The depolymerized chondroitin polysulfate can be precipitated with methanol, if necessary after addition of a neutral salt and adjustment of the pH value to within the range from 3 to 14, in particular from 6 to 10.

Crude chondroitin polysulfates which differ greatly in purity and coloration are suitable for use in the present process. In spite of the depolymerization operation, which greatly lightens the color, it may be necessary to include a decoloration step or a bleaching step before further processing. Bleaching is carried out with peracetic acid. The following conditions have been found to be advantageous: the pH range can be from 2.5 to 14, preferably from 3 to 11. The peracetic acid concentration can be 0.1-10%, preferably 1-5%. The concentration of the crude chondroitin polysulfate can be 2-40%, preferably 5-25%. The reaction is carried out in the temperature range from 0° to 100° C., preferably from 15° to 70° C. The reaction time can be between 1 minute and 96 hours, in particular between 1 and 24 hours.

According to a preferred embodiment, the peracetic acid treatment can be incorporated in the subsequent molecular fractionation process. As has already been mentioned above, the peracetic acid treatment can also be omitted completely.

The molecular weight range from about 5,000 to 15,000 is fractionated out of the product obtained after the bleaching or depolymerization step by precipitation with methanol at various concentrations.

For this step, the depolymerized and, if necessary, bleached chondroitin polysulfate can be treated in aqueous solution with methanol in the presence of a neutral salt as follows (1st precipitation with methanol): the concentration of the depolymerized chondroitin polysulfate in the aqueous solution can be 5-30%, preferably 5-20%. The pH value can be in the range from 2 to 10, preferably from 3.0 to 7.5. The neutral salt content can be 0.5-10%, preferably 1-5%. A preferred neutral salt is sodium chloride. The temperature can be in the range from 0° to 50° C., preferably from 15° to 30° C. The amount of methanol can be 25-45% by volume, preferably 30-40% by volume, relative to the entire treatment medium. High-molecular and highly sulfated chondroitin polysulfate entities are precipitated, together with impurities, and can be removed by filtration or centrifugation.

The methanol-containing solution which remains is brought to a methanol concentration of 60-85% by volume, preferably 75-80% by volume, relative to the entire treatment medium, by further addition of methanol (2nd precipitation with methanol), and a chondroitin polysulfate precipitate from which the very low-molecular and low-sulfated components are removed, together with impurities, is obtained; these components are not precipitated.

The entire fractionation process with methanol or a part thereof can be replaced by ultrafiltration. For example, by ultrafiltration of aqueous solutions of depolymerized chondroitin polysulfate with membranes with an exclusion limit of 6,000 and above (for example membranes of cellulose acetate, polyamide or polysulfone), it is possible to retain the same first fraction as described above in the retained material. The concentration of the chondroitin polysulfate solution can be 1-10%, preferably 1-5%. The pH value of the solution can be 2-14, preferably 5-10. The permeate can be freed from low-molecular chondroitin polysulfate components by precipitation with methanol as described above.

This effect can also be achieved by a second subsequent ultrafiltration with membranes with an exclusion limit of 8,000 and below. The concentration of the chondroitin polysulfate solution can be 1 to 10%, preferably 1 to 5%. The pH value of the solution can be 2 to 14, preferably 5 to 10.

The exclusion limit for substances of a certain molecular weight given by the manufacturers of ultrafiltration membranes in most cases does not apply to chondroitin polysulfates. The suitable membrane in an individual case must therefore be established by experiment, but experience shows that it is within the ranges indicated.

The removal of salts, if necessary heavy metal ions, and impurities is achieved by treatment with a cation exchanger. The metal ions are bonded by exchanger resins in the protonated form and the free mucopolysaccharide-polysulfuric acid passes into the filtrate or eluate. The treatment can be carried out at a temperature from 0° to 50° C., and advantageously at room temperature. It can be carried out by the batch method by stirring in the cation exchanger, or by the continuous or discontinuous column technique. Suitable ion exchanger resins are strongly acid products, such as, for example, Lewatit S 100, Dowex X 50 or Amberlite IR 120 in the protonated form.

The batch method is carried out in aqueous solution with chondroitin polysulfate concentrations of 2-20%, in particular 5-15%. The amount of ion exchanger resin can be 2-10 parts by volume, in particular 3-8 parts by volume, relative to 1 part by weight of chondroitin polysulfate dry substance. The removal of salts can also be carried out under the same conditions using exchangers poured into columns.

The strongly acid filtrate or eluate from the demineralization step is subjected to precipitation with 2.5-6 parts by volume, preferably 3-4 parts by volume, of methanol in the presence of 0.5-5% of a neutral salt, in particular 0.5-3% of sodium chloride. During the precipitation from an acid medium, free sulfuric acid and low-molecular chondroitin polysulfate components as well as impurities remain in solution. After the chondroitinpolysulfuric acid precipitate has been separated off, it can be either reprecipitated from neutral solution or further used directly for the subsequent process step whilst still methanol-moist.

Demineralization can be omitted if ultrafiltration has been carried out using an ultrafiltration membrane with a low exclusion limit (2nd ultrafiltration), in which case the retained material is further processed.

For further lightening of the color and in order to achieve a particularly good color stability during heat sterilization of the pure chondroitin polysulfate, demineralization can be followed by a further purification step.

Treatment of chondroitin polysulfate solutions with active charcoal and complete removal of the adsorbate gives a chondroitin polysulfate solution from which, after the pH has been adjusted, the product is precipitated with methanol in the presence of a neutral salt. The concentration of the aqueous chondroitin polysulfate solution to be treated is 5-25%, in particular 10-20%. Its pH value is 4-10, in particular 5-8. 0.1-3 parts by weight of active charcoal (relative to one part by weight of chondroitin polysulfate) are employed. The temperature can be 20°-100° C. The treatment time is 10-180 minutes.

The active charcoal is separated off. Fine filtration through a membrane filter is then advisable, in order to obtain a completely charcoal-free solution. The pH value is adjusted to 6-10, in particular 7-8, and the end product is precipitated with methanol in the presence of a neutral salt, for example sodium chloride in a concentration of 0.5-5%, in particular 1-2%. The final concentration of methanol is adjusted to 60-85% by volume, preferably 75-80% by volume. Examples of suitable active charcoals are Brilonit normal (Lurgi), active charcoal pure, Cat.No. 2183 (Merck), active charcoal pure, powder, Cat.No. 18003 (Riedel de Haen). Whether decoloration with active charcoal is carried out depends on the chondroitin polysulfate used as the starting material.

It may be advantageous to carry out the precipitation of the purified chondroitin polysulfate with methanol in the presence of a complexing agent and/or sodium pyrosulfite. This measure is particularly expedient in the case of the end product. As a result thereof, injection solutions which contain chondroitin polysulfate and which, when stored, are free from turbidity and subsequently darken only unnoticeably remain. Examples of complexing agents which are used are nitrilotriacetic acid, ethylenedinitrilotetraacetic acid, 1,2-cyclohexylenedinitrilotetraacetic acid, diethylenetriaminepentaacetic acid and 3,6-dioxaoctamethylenedinitrilotetraacetic acid, in concentrations of 0.01-0.5%. Concentrations of 0.05-0.35% are preferably used. The concentration of the sodium pyrosulfite which may be used during the precipitation with methanol can be 0.01-0.5%.

The chondroitin polysulfate described is of therapeutic significance in humans and animals. The substance has an anticoagulemic, thrombolytic, thromboprophylacetic (especially on the deep venous thromboses), antiatherosclerotic, antilipemic, antiinflammatory, antiexudative, antiarthrotic and virustatic action.

A characteristic novel substance which is distinguished by a surprisingly low toxicity is obtained by the particular course and the nature of the treatments of the process according to the invention.

TABLE 1

| Animal species | Acute toxicity Administration | $LD_{50/7d}$ |
| --- | --- | --- |
| NMRI mice | i.v. | >3,500 mg/kg |
| Wistar rats | i.v. | >3,000 mg/kg |
| Cats | i.v. | >1,000 mg/kg |
| Dogs | i.v. | >1,000 mg/kg |

The invention thus also relates to a chondroitin polysulfate with an acute toxicity corresponding to a lethal dose, on intravenous administration, of >3,500 mg/kg in NMRI mice, of >3,000 mg/kg in Wistar rats and of >1,000 mg/kg in cats and dogs. A preferred product according to the invention has an acute toxicity corresponding to a lethal dose, on intravenous administration, of >4,000 mg/kg in NMRI mice, of >3,500 mg/kg in Wistar rats, of >1,500 mg/kg in cats and of >1,000 mg/kg in dogs.

Chondroitin polysulfates with a $LD_{50}$ (mice, i.v.) of only 1,000 mg/kg have so far been described in the literature. The process according to the invention thus permits the preparation of chondroitin polysulfate with a considerably wider therapeutic range.

In particular, the chondroitin polysulfate prepared by the process according to the invention displays the following parameters:

nitrogen: 1.65-2.00%
sulfur: 12.5-14.5%
hexuronic acid: 0.98-1.22 mmoles/g
hexosamine: 0.96-1.24 mmoles/g Finally, the invention relates to a pharmaceutical composition, which is characterized in that it contains a chondroitin polysulfate which can be prepared by the process according to the invention or a chondroitin polysulfate as has been defined above.

Experiments have shown that single dosages of between 20 and 250 mg, in particular between 30 and 150 mg, per individual in 0.2-2.0 ml, in particular 0.2-1.0 ml have a therapeutic action in humans and are well tolerated. Daily doses of up to 500 mg prove to be therapeutically advantageous. The injection can be intramuscular, intraarticular, subcutaneous or intravenous, without the doctor being tied specifically to only these types of injection. Therapeutically usable solutions of the active compound can be packed, for example, in ampoules, ready-to-use syringes, pierceable bottles, phials for injection guns and other primary means of packing appropriate for the injection. Other methods of administration are peroral, percutaneous, rectal, sublingual or buccal administration. The preferred dosage corresponds to that for administration by injection.

The chondroitin polysulfate obtained according to the invention is also suitable for use in veterinary medicine, in which it shows the actions described. The dosage for dogs is between 0.1 and 5 mg/kg of body weight and day, preferably 0.5 to 1.5 mg/kg, in a volume of 0.1-10 ml, in particular 0.5-1.0 ml. In the case of horses, for example, *single daily doses of 100-1,000 mg, preferably 150-500 mg, in 0.1-20 ml, in particular 1-5 ml*, prove to be suitable. The chondroitin polysulfate can be administered in the same manner as to humans.

The following method was used to determine the mean molecular weight:

A 20 mg sample is chromatographed into 2M sodium chloride solution on a Biogel P 10 column (50 g; H=100 cm, $\phi=2$ cm). The chondroitin polysulfate is detected in the 10 ml fractions collected, by hexuronic acid determination in accordance with the method of Z. Dische: J.Biol. Chem. 167, 189 (1947) modified by J. D. Gregory: Arch, Biochem. Biophys. 89, 157 (1960). Chondroitin polysulfate fractions in which the molecular weight has been determined by ultracentrifugation are used as standards. The mean molecular weight is calculated from the volume of eluate in which 50% of the total amount of hexuronic acid found in the chromatogram is eluted.

The following examples illustrate the invention.

EXAMPLE 1a (Stage A)

7.5 kg of crude chondroitin polysulfate (obtainable according to German Patent Specification 870,094) are dissolved in 75 liters of hot water, and 2.25 kg of sodium chloride and 2 ml of octan-1-ol are added. A solution of 75 g of ethylenedinitrilotetraacetic acid in 750 ml of 1N sodium hydroxide solution is now added. The mixture is heated to 95° C. and 7.5 liters of 30% strength hydrogen peroxide solution are then stirred in. The temperature is kept between 90° and 95° C. for 100 minutes and the mixture is then cooled rapidly to room temperature.

1.5 kg of sodium chloride are dissolved in the reaction mixture, 360 liters of methanol are stirred in and, after 30 minutes, the clear supernatant liquor is decanted off and the precipitate is filtered off over a suction filter. The material on the filter is washed with methanol and dried at a temperature below 60° C. About 7 kg of depolymerized chondroitin polysulfate are obtained.

EXAMPLE 1b (Stage A)

7.5 kg of crude chondroitin polysulfate are dissolved in 22.5 liters of water, and first 1.5 kg of sodium chloride and then a solution of 37.5 g of copper-II sulfate pentahydrate in 750 ml of water are added. 3 liters of 30% strength hydrogen peroxide are added, with cooling, and the mixture is kept at 25° C. for 5 hours. It is then adjusted to pH 10.5 with 30% strength sodium hydroxide solution, precipitation is effected with 132 liters of methanol, with stirring, the supernatant liquor is decanted off and the precipitate is filtered off with suction. The material on the filter is washed with methanol and dried at a temperature below 60° C. About 6.8 kg of depolymerized chondroitin polysulfate are obtained.

EXAMPLE 1c (Stage A)

9 kg of crude chondroitin polysulfate are dissolved in 45 liters of water, a solution of 8.57 g of cobalt-II chloride hexahydrate in 1 liter of water is added and the mixture is made up to 67 liters with water. 1.35 liters of 40% strength peracetic acid are added at room temperature in the course of 2 hours, with continuous stirring. A solution of 27 g of disodium ethylenedinitrilotetraacetate dihydrate in 1 liter of water is then added. The pH is now adjusted to 11 with 30% strength sodium hydroxide solution, 2.2 kg of sodium chloride are added and precipitation is carried out with 290 liters of methanol, with stirring. After one hour, the supernatant liquor is decanted off, the precipitate is filtered off on a suction filter and the material on the filter is washed with methanol and dried at a temperature below 60° C. About 8.4 kg of depolymerized chondroitin polysulfate are obtained.

EXAMPLE 2

(Stage B)

8.0 kg of depolymerized chondroitin polysulfate are dissolved in 74 liters of water, the solution is mixed with 2 liters of 40% strength peracetic acid, the pH value is adjusted to 8 with 30% strength sodium hydroxide solution and the mixture is left to stand at room temperature for 24 hours. 0.4 kg of sodium chloride is dissolved in the mixture and precipitation is carried out with 320 liters of methanol. The precipitate is filtered off, washed with methanol and dried. About 7.9 kg of white material are obtained.

EXAMPLE 3a (Stage C)

6.3 kg of depolymerized chondroitin polysulfate are dissolved in 27.1 liters of hot water, 3.15 liters of 40% strength peracetic acid are added, the components are mixed and the mixture is left to stand for 4 hours. 45.4 liters of water are then added, 2.1 kg of sodium chloride are dissolved in the mixture and the pH value is adjusted to 10.5 with 30% strength sodium hydroxide solution. In order to obtain a methanol concentration of 36.5% by volume in the mixture, 0.5748 liter of methanol per liter of solution are then stirred in, that is to say, for example 48.6 liters of methanol. The precipitation mixture is left to stand overnight and the supernatant liquor is then decanted off and the semiliquid precipitate is centrifuged off. The clear supernatant liquor, for example 128.5 liters, is stirred with 2.175 liters of methanol per liter of solution, that is to say, for example, 279.5 liters of methanol, so that a final methanol concentration of 80% by volume is achieved. The precipitate is allowed to settle for 1 hour, the supernatant liquor is decanted off and the residual suspension is filtered with suction. The precipitate is washed with methanol and dried at a temperature below 60° C. About 5.6 kg of intermediate are obtained.

EXAMPLE 3b (Stage C)

2 kg of depolymerized chondroitin polysulfate are dissolved in 200 liters of water and the solution is filtered through a sterile filter and subjected to ultrafiltration under a pressure of 2.8 bars at 32° C. using a plate ultrafiltration apparatus (membrane area: 2.25 m², exclusion limit stated for the cellulose acetate membrane: molecular weight of 15,000). The solution is pumped round at a flow rate of 6.5 m³/hour. When the volume of retained material is about 20 liters, this material is subjected to ultrafiltration 3 times, after being mixed with 50 liters of water each time.

The combined permeates are subjected to ultrafiltration using a cellulose acetate membrane with a stated molecular weight exclusion limit of 6,000, but otherwise under identical conditions to those above. The retained material is concentrated down to a concentration of 10%, sodium chloride is added up to a concentration of 0.5%, the pH value is adjusted to 7.5 and precipitation is carried out with 4 parts by volume of methanol, with stirring. After washing the precipitate which has been filtered off with suction, it is dried. The resulting intermediate weighs 1.78 kg.

EXAMPLE 4a (Stage D)

5.4 kg of the intermediate from process step 3 are dissolved in 54 liters of water, 21.6 liters of strongly acid cation exchanger (for example Lewatit S 100) in the protonated form are stirred in and the mixture is stirred at room temperature for 1 hour. The cation exchanger is filtered off with suction and rinsed twice with 8.1 liters of water each time and the filtrates are combined. 2.19 kg of sodium chloride are added to the filtrate and precipitation is carried out with 292 liters of methanol, with stirring. The precipitation batch is left to stand overnight and the supernatant liquor is then decanted off, the suspension which remains is filtered with suction and the material on the filter is washed out thoroughly with methanol. The precipitate is dissolved in 43.2 liters of water, the pH value is adjusted to 7.5 with 30% strength sodium hydroxide solution, 700 g of sodium chloride are added and precipitation is carried out with 139.2 liters of methanol, with stirring. The clear supernatant liquor is decanted off, the residual suspension is filtered through a suction filter and the material on the filter is washed with methanol. After drying, 3.6 kg of demineralized chondroitin polysulfate are obtained.

EXAMPLE 4b (Stage D)

9 kg of the intermediate obtained after process step, or the still methanol-moist precipitate from this process step, are dissolved in an amount of water such that 90 liters of solution are obtained. This solution is allowed to run through an ion exchanger column filled with 36 liters of the cation exchanger Amberlite IR 120 in the H+ form. The ratio of the height to which the column is filled to the diameter is, for example, about 2.5:1. When the substance solution has run through, the column is rinsed with 33.3 liters of water. 3.7 kg of sodium chloride are added to the combined filtrates containing the substance and precipitation is effected by addition of 492 liters of methanol. The precipitate is filtered off with suction and washed with methanol and the still solvent-moist precipitate is dissolved in pyrogen-free water to give a total volume of 72 liters. 1.15 kg of sodium chloride are added, the pH value is adjusted to 7.5 with 30% strength sodium hydroxide solution and precipitation is carried out with 219 liters of methanol. The precipitate is filtered off with suction, washed with methanol and dried. About 6 kg of demineralized chondroitin polysulfate are obtained.

EXAMPLE 5

(Stage E)

20 kg of demineralized chondroitin polysulfate are dissolved in 190 liters of pyrogen-free water. The solution is heated to 90° C. and 40 kg of active charcoal are added (Riedel de Haen No. 18003). The temperature is kept at 90° C. for 60 minutes and the mixture is then filtered whilst still hot using a pressure filter. The charcoal residue is washed twice with 40 liters each time of pyrogen-free water, and the filtrates are combined. 3 kg of sodium chloride and 660 g of disodium ethylenedinitrilotetraacetate dihydrate are added. The pH value is adjusted to 7.5. The mixture is then filtered through a pre-washed membrane filter (pore diameter: 0.2 μm). The completely clear solution is subjected to precipitation with 720 liters of methanol, with stirring. The precipitate is filtered off with suction, washed with methanol and dried at a temperature below 50° C. About 18 kg of white, fine-particled, pure, injectable chondroitin polysulfate are obtained. Investigation by chemical analysis gives the following substance values:

N: 1.77%
S: 12.96%
hexuronic acid: 1.08 mmoles/g
hexosamine: 1.12 mmoles/g

EXAMPLE 6

(Preparation of an injection solution)

3.25 kg, calculated relative to anhydrous substance, of pure chondroitin polysulfate and 0.325 kg of sodium chloride are dissolved in about 50 liters of aqua pro iniectabilia, with stirring, and the solution is made up to 65 liters. After the pH value has been adjusted to 8.4 with N sodium hydroxide solution and the solution has been subjected to sterile filtration through a membrane filter, the solution is filled into ampoules under sterile precautions in a known manner. The sealed ampoules are exposed to heat treatment in a boiling water bath for 60 minutes.

I claim:

1. A process for the preparation of an injectable chondroitin polysulfate with a molecular weight up to about 15000 which comprises:
    A. oxidatively depolymerizing crude chondroitin polysulfate by treatment with an oxidatively depolymerizing agent selected from the group consisting of
        (a) peracetic acid in the presence of salts of heavy metals, and
        (b) hydrogen peroxide; and
    B. fractionating the oxidatively depolymerized chondroitin polysulfate so produced by a step selected from the group consisting of
        (a) precipitation with methanol, ethanol, isopropanol, acetone, tetrahydrofuran or dioxane; and
        (b) ultrafiltration.

2. A process according to claim 1, wherein the oxidative depolymerization with hydrogen peroxide is carried out in the presence of a complexing agent selected from the group consisting of nitrilotriacetic acid; ethylenedinitrilotetraacetic acid; 1,2-cyclohexylenedinitrilotetraacetic acid; diethylenetriamine pentaacetic acid and 3,6-dioxaoctamethylenedinitrilotetraacetic acid.

3. A process according to claim 1, wherein the oxidative depolymerization with hydrogen peroxide is carried out in the presence of salts of heavy metals selected from the group consisting of iron, cobalt, copper, manganese and vanadium.

4. A process according to claim 1, wherein the oxidative depolymerization with peracetic acid is carried out in the presence of salts of heavy metals selected from the group consisting of iron, cobalt, manganese and vanadium.

5. A process according to claim 4, wherein the concentration of heavy metal salts is maintained between 0.001 and 0.5% by weight based on the volume of liquids present.

6. A process according to claim 3, wherein the concentration of heavy metal salts is maintained between 0.001 and 0.5% by weight based on the volume of liquids present.

7. A process according to claim 1, which further comprises bleaching the oxidatively depolymerized chondroitin polysulfate with peracetic acid before fractionating.

8. A process according to claim 1, wherein the fractionation is carried out by a step selected from the group consisting of:
(a) two precipitations,
(b) two ultrafiltrations,
(c) one precipitation and then one ultrafiltration, and
(d) one ultrafiltration and then one precipitation.

9. A process according to claim 1, which comprises one fractionation step.

10. A process according to claim 8, wherein the first precipitation is carried out with methanol in a concentration between 25 and 40% by volume based on the volume of liquids present.

11. A process according to claim 8, wherein the second precipitation is carried out with methanol in a concentration between 60 and 85% by volume based on the volume of the liquids present.

12. A process according to claim 8, wherein the first fractionation is carried out by ultrafiltration with a membrane with an exclusion limit of at least 6000.

13. A process according to claim 8, wherein the second fractionation is carried out by ultrafiltration with a membrane with an exclusion limit of at least 8000.

14. A process according to claim 1, which further comprises treating the depolymerized chondroitin polysulfate with cation exchangers after the fractionation.

15. A process according to claim 1, which further comprises decolorizing the oxidatively depolymerized chondroitin polysulfate with active charcoal after the fractionation.

* * * * *